(12) United States Patent
Hawkes et al.

(10) Patent No.: US 6,870,177 B2
(45) Date of Patent: Mar. 22, 2005

(54) SHADOW-CREATING DEPRESSION FOR ESTABLISHING MICROCHIP LOCATION DURING VISUAL INSPECTION

(75) Inventors: Malcolm V. Hawkes, Escondido, CA (US); Jon Stuart Wright, San Marcos, CA (US); Robert S. Burgoyne, Oceanside, CA (US); Jeffrey L. Fish, San Diego, CA (US)

(73) Assignee: Electro Scientific Industries, Inc., Portland, OR (US)

(*) Notice: Subject to any disclaimer, the term of this patent is extended or adjusted under 35 U.S.C. 154(b) by 90 days.

(21) Appl. No.: 10/294,335

(22) Filed: Nov. 14, 2002

(65) Prior Publication Data

US 2003/0097877 A1 May 29, 2003

Related U.S. Application Data

(60) Provisional application No. 60/333,690, filed on Nov. 27, 2001.

(51) Int. Cl.[7] .............................................. G01N 21/86
(52) U.S. Cl. ................................................ 250/559.36
(58) Field of Search ..................... 250/559.45, 559.29, 250/559.3, 559.36, 559.37

(56) References Cited

U.S. PATENT DOCUMENTS

| 4,312,117 A | | 1/1982 | Robillard et al. ............. 29/589 |
| 4,953,283 A | * | 9/1990 | Kawabata et al. ............ 29/593 |
| 5,088,190 A | | 2/1992 | Malhi et al. .................. 29/843 |
| 5,123,850 A | | 6/1992 | Elder et al. ................... 439/67 |
| 5,543,725 A | | 8/1996 | Lim et al. .................... 324/755 |

* cited by examiner

*Primary Examiner*—Thanh X. Luu
(74) *Attorney, Agent, or Firm*—Stoel Rives LLP

(57) ABSTRACT

An apparatus for accurately locating a micro-electronic chip in a chip-holding cavity for visual testing, the chip having at least a front wall and a pair of opposed, spaced-apart side walls, wherein the front wall meets with each of the side walls to form opposed, spaced-apart first and second front edges, comprising a cavity side wall formed to juxtapositionally abut at least one of the side walls of the chip, the cavity side wall having formed therein a depression creating a shadow projecting forward from the depression, wherein the first front edge of the chip forms a border of the shadow to form an objectively measurable contrast in grayness between the shadow and the chip.

44 Claims, 5 Drawing Sheets

Grayscale Steps from Black to White

SHADOW-CREATING DEPRESSION FOR ESTABLISHING MICROCHIP LOCATION DURING VISUAL INSPECTION

This application claims the benefit of U.S. Provisional Application No. 60/333,690 filed Nov. 27, 2001.

BACKGROUND OF THE INVENTION

1. Field of the Invention

This invention relates to the field of visual inspection and testing of micro-electronic chips. More particularly, the invention pertains to an apparatus for expediently locating the chip, seated in a cavity, to begin an accurate visual analysis of its surfaces.

2. Description of the Prior Art

The recent downsizing of micro-electronic chips and the high demand for these chips, necessitates the need for fast, accurate and economical testing of their physical and electrical properties. In order to test the chips more efficiently, it is necessary to first eliminate visibly flawed chips from the production line so that later electrical testing is conducted only on visibly acceptable chips. Examples of such visually observable flaws are delamination of the dielectric body, cracks in the chip's exterior and flaws in the metal termination such as smears, and spillovers, and unacceptable waviness. Visual inspection apparatuses are used in the industry to test these physical properties. These apparatuses generally include camera devices for observing the chip, software processing devices for detecting and recording the flaws, and bright light sources, for illuminating the chip.

Prior art visual inspection devices have not been able to accurately and efficiently observe the chip because of high specularity values of the chip and surrounding materials. Specularity of a material describes the size and brightness of specular highlights it reflects. Smooth, reflective objects have highlights that are small and bright. Rough, reflective objects have highlights that are large and diffuse, but still bright. Less reflective objects, rough or smooth, have dimmer highlights. Usually, conventional metallic materials, such as aluminum, stainless steel, titanium etc., that are used to make load wheels to house the chip during the visual inspection process, create significant specular highlights due to normal wear and tear and accumulation of foreign matter on the metals. Certain treatments and coatings can be used to reduce the apparent specularity of these surfaces but these remedies are temporary and deteriorate over time. The replacement of these metals with plastic-based or other similar materials is ineffective because the inherent weaker physical properties of the plastic materials will cause them to wear out over time.

The high degree of specularity around the exposed surface of the chip and its surrounding environment, makes it difficult to electronically visualize exactly where the chip is located in the chip-holding cavity in order for the software program to start the visual test on the chip. The brightness and light reflection of the surrounding environment blend with that of the chip and makes it virtually impossible to accurately distinguish the chip from the rest of its environment, especially under high speed processing conditions where residence time of the chip in the cavity is measured in microseconds. Therefore, absent a point of reference, the software program cannot start visual testing of the chip, or may start the visual testing process at an erroneous point of reference.

SUMMARY OF THE INVENTION

This invention is an apparatus for creating a dark, basically black, shadow that is strategically placed to abut at least a portion of an edge of a chip for providing contrast between the edge of the chip abutting the shadow and the shadow. The portion of the edge of the chip abutting the shadow forms a line of contrast to provide an inspection device with a point of reference to start its visual inspection. This invention overcomes the problems set forth above with regard to the prior art visual inspection methods. This invention is useful specifically with a metalized, right-rectangular, parallelepiped, micro-electronic chip that has at least two opposed, spaced-apart front edges that are formed by the respective meeting of a front wall and two opposed, spaced-apart side walls. This chip is of the type used throughout the computer industry today.

This inventive apparatus includes a cavity, preferably a plurality thereof, located in a rim of a chip-handling means, such as about the periphery of a chip-handling wheel, for receiving the chips. The cavities are of the shape and size to receive a single chip in an upright position, and momentarily holding the chip to allow an inspection apparatus to inspect and test the outer surface of the chip. The cavity includes at least one cavity side wall and may have a cavity rear wall which is formed perpendicular to the cavity side wall, for assisting in holding the chip in the cavity. The cavity side wall abuts a portion of at least one of the side walls of the chip when the chip is properly seated.

In another embodiment of this invention, part of the cavity side wall is formed into a recess including a first wall that extends away from the cavity. The recess is located adjacent the side wall of the chip. The recess reduces the amount of specularity and light reflection around the front edge of the chip to reduce interference with detecting the edge of the chip by the inspection device.

An observable depression is formed within at least the cavity side wall and the first wall. The depression is deep enough to appear as a very dark, basically black, background, creating an objectively measurable contrast in grayness between the depression and the chip. The chip is located in the cavity in a position where at least a portion of at least one of the front edges of it forms a border, preferably straight and vertical, of the black shadow or background, and thus, forms a distinct line of contrast between the front edge of the chip and the dark-shadowed depression. The depression may be circular, oval-shaped, or may be a horizontal slot that extends away from the cavity. The shape of the depression may be determined by various factors such as the size of the cavity holding the chip and the size of the chip.

In a different embodiment of this invention, the depression may further extend along the cavity side wall and along the cavity rear wall to create a shadow therein that is eclipsed by the other front edge of the chip. The shadow that is created forms an objectively measurable contrast in grayness between the shadow and the chip. A distinct line of contrast is formed where the other front edge of the chip eclipses the dark shadow of the depression in the cavity rear wall.

The depression is black under the lighting conditions which is in contrast to the grayness of the chip and the handling wheel. The recess located adjacent the chip also reduces the specularity of the surrounding environment. The line of contrast locates the chip. Therefore, because of the stark contrast between the shadow in the depression and the chip, the inspection device can efficiently and expediently detect the edge of the chip to start the visual testing of the chip.

During the inspection process, the chip is held in one position by a vacuum means for a long enough period to be tested by the inspection device where the inspection device may include a coupled-charged device, a software inspection unit and an illumination source.

Accordingly, the main object of this invention is a shadow-creating apparatus that assists a software inspection device to accurately locate the chip to start the visual testing process. Other objects of the invention are an apparatus that surpasses temporary surface treatments and coatings; that is simplistic and economical to manufacture and maintain; that can be produced to accommodate chips of all shapes, sizes and configurations; that can easily be used with the current visual inspection apparatuses available in the industry today; and that has a high production rate yielding a better end product because of the visual inspection apparatus' ability to swiftly and accurately locate the chips within the cavity.

These and other objects of the invention will become more apparent when reading the description of the preferred embodiment along with the drawings that are appended hereto. The protection sought by the inventor may be gleaned from a fair reading of the claims that conclude the specification.

DESCRIPTION OF THE PREFERRED EMBODIMENT

Figure 1:
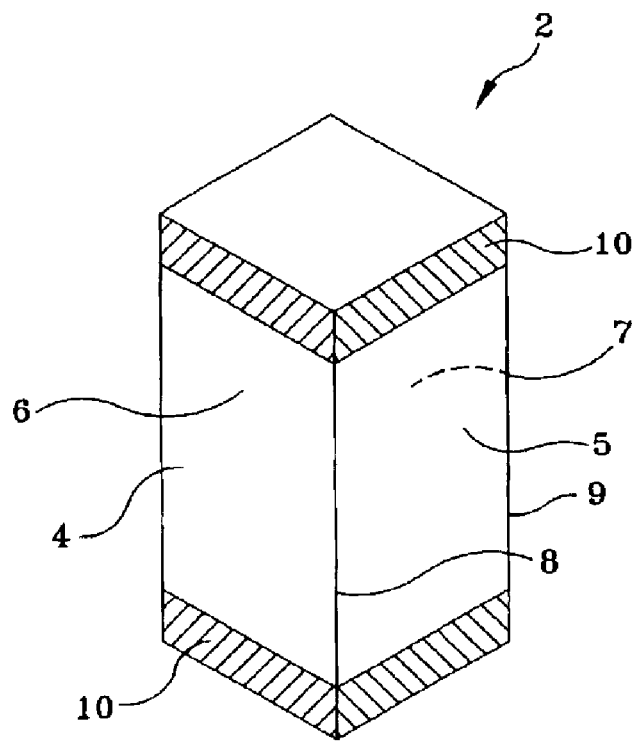
FIG. 1 is a perspective view of the right-rectangular, parallelepiped, micro-electronic chip to which this invention is directed.
Figure 2:
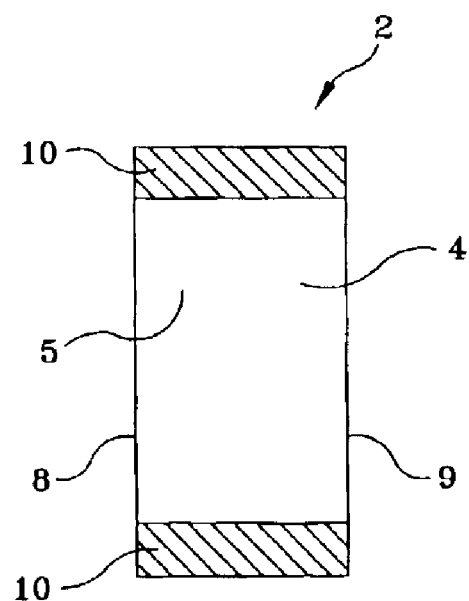
FIG. 2 is a front view of the chip showing the first and second front edges to be located by this invention.

Turning now to the drawings wherein elements or limitations are identified with numbers and like elements or limitations are identified with like numbers throughout the twelve figures, FIGS. 1 and 2 show a micro-electronic chip 2 to which this invention is directed, and which generally includes a rectangular-shaped, solid, enclosed body 4 comprising at least a front wall 5 and a pair of opposed, spaced-apart, side walls 6 and 7, where front wall 5 meets with each of side walls 6 and 7 to form respective, opposed, spaced-apart first front edge 8 and second front edge 9. Chip 2 used with this invention, has a pair of metalized, spaced-apart, terminal ends 10 for connecting to a circuit board. Chip 2 may also be parallelepiped in angles larger or smaller than 90 degrees and may be of different sizes. The right-rectangular, parallelepiped chip, however, is the industry standard and is the product to which this invention is primarily directed.

Figure 3:
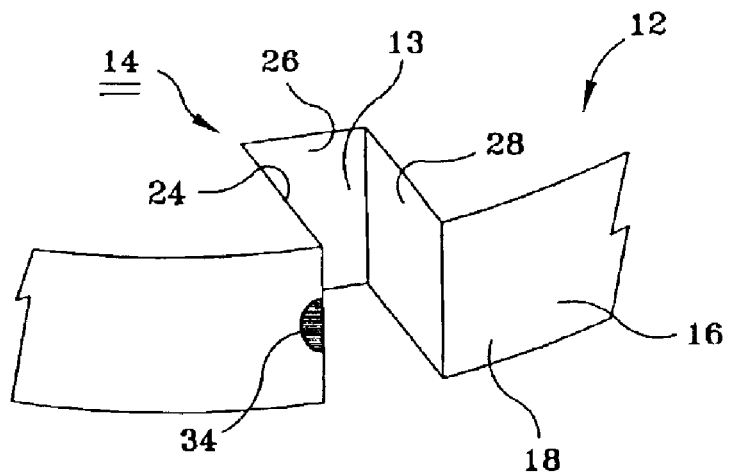
FIG. 3 is a perspective view of a typical cavity formed within a typical chip-handling wheel showing a cavity side wall wherein an observable shadow-creating depression is formed according to the teaching of this invention.
Figure 8:
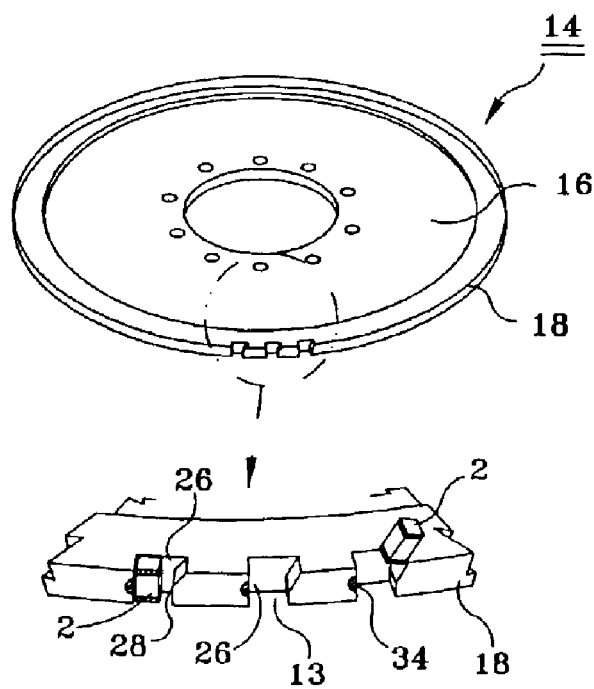
FIG. 8 is a perspective view of the chip-handling wheel with a broken out view of a portion of the wheel showing the relationship of the depression, the cavity, the cavity side wall, and the chip seated within the cavity.

As shown in FIGS. 3 and 8, the apparatus 12 of this invention includes a cavity or pocket 13 formed in a chip-handling means 14, such as a chip-handling wheel 16, for receiving an inventory of chips 2, so that chips 2 can be arranged to be inspected and tested. Chip-handling means 14 is similar to the one shown in U.S. Pat. No. 6,294,747 and includes a chip-handling wheel 16, particularly, a chip-loading wheel, having an outer rim 18. Chip-handling wheel 16 has at least one cavity 13, but preferably a plurality thereof, formed in outer rim 18 for receiving chips 2, and are of the shape and size to receive a single chip 2 in an upright position in each cavity 13.

Figure 4:
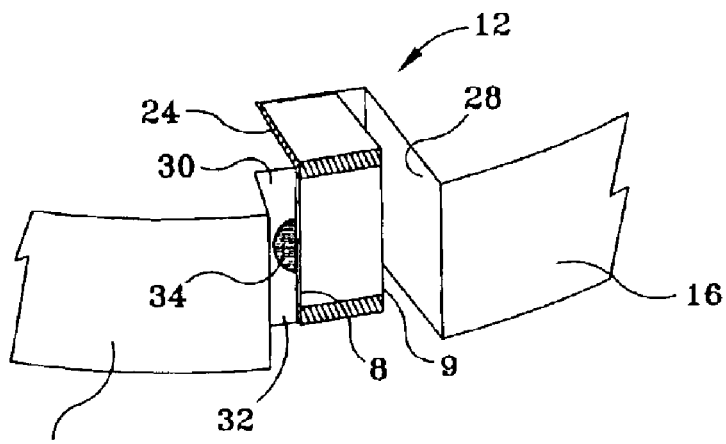
FIG. 4 is a perspective view of another cavity showing the cavity side wall and a first wall having formed therein the shadow-creating depression.
Figure 5:
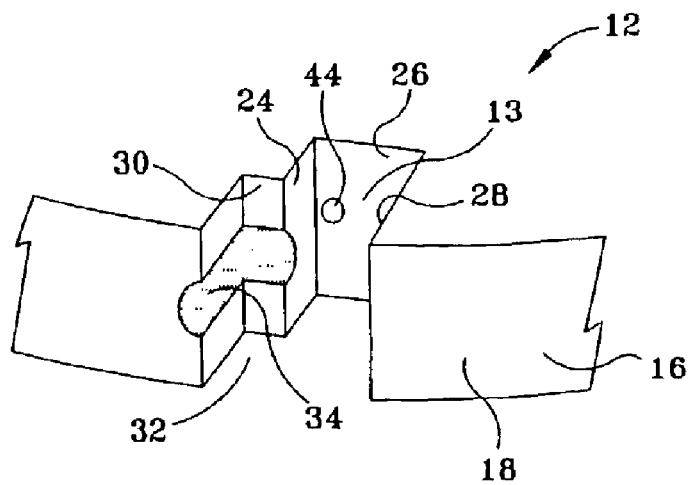
FIG. 5 is a perspective view of still another cavity showing the cavity side wall and the first wall wherein a horizontal slot is formed that extends further into the wall.
Figure 6:
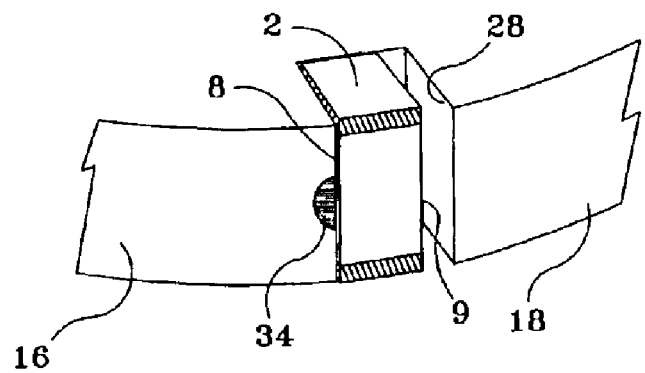
FIG. 6 is a perspective view of the chip shown in FIG. 1 seated within the cavity.

As shown in FIGS. 3, 7a, 7b, and 7c, cavity 13 is bound by at least one cavity side wall 24 formed to juxtapositionally abut at least a portion of side wall 6 of chip 2 when chip 2 is properly seated in cavity 13. Cavity 13 may further be bound by a cavity rear wall 26, which is preferably formed at a perpendicular angle with cavity side wall 24. Another cavity side wall 28, spaced-apart from first side wall 24, is formed for aiding chip 2 being placed within cavity 13. Cavity 13 may also have a bottom surface (not shown) upon which chip 2 may rest. As shown in FIGS. 4 and 5, another embodiment of the invention shows cavity side wall 24, that abuts the portion of side wall 6 of chip 2, be partially formed into a first wall 30 that extends away from cavity 13. A recess 32 is formed where first wall 30 extends away from cavity 13. Recess 32 is located adjacent side wall 6 of chip 2.

Figure 7A:
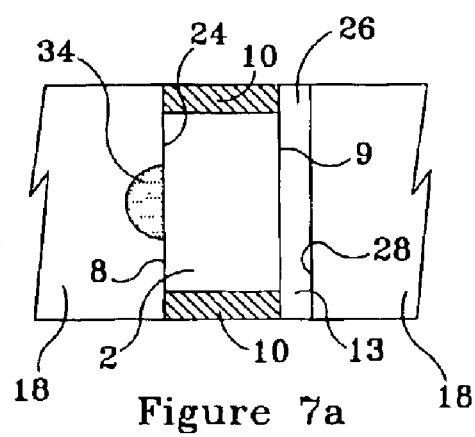
FIG. 7a is a front view of the chip seated within the cavity shown in FIG. 6 showing the first front edge forming a border of the shadow created by a circular depression.
Figure 7B:
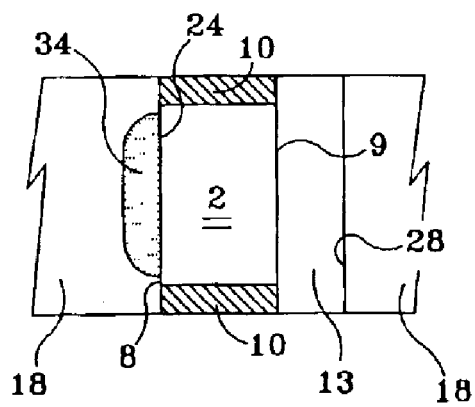
FIG. 7b is a front view of the chip seated within the cavity shown in FIG. 6 showing the first front edge forming a border of the shadow created by an oval depression.
Figure 7C:
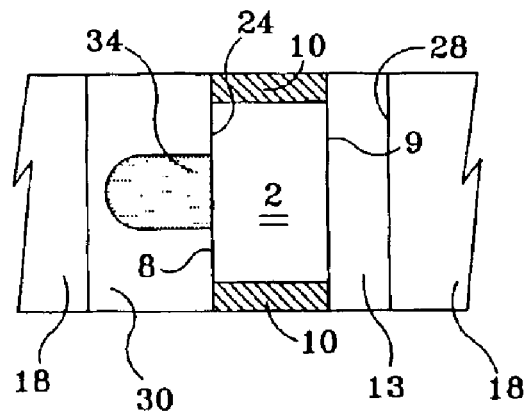
FIG. 7c is a front view of the chip seated within the cavity shown in FIG. 6 showing the first front edge forming a border of the shadow created by a horizontal slotted depression.
Figure 9:
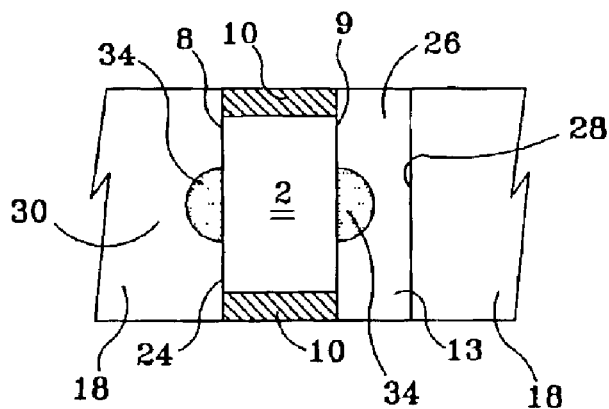
FIG. 9 is a front view of the chip seated within the cavity showing the second front edge eclipsing the shadow created by the depression formed along the rear wall of the cavity; and, FIG. 10 is a perspective view of a typical vacuum means.

As shown in FIGS. 4, 5, and 7, a depression 34 is formed in cavity side wall 24, wide enough and deep enough to project a black shadow forward from the side of cavity 13 and creating an objectively measurable contrast in grayness between depression 34 and chip 2. Chip 2 is located in cavity 13 in a position where at least a portion of first front edge 8 forms a border, preferably straight and vertical, of the black shadow or background, and thus, forms a distinct line of contrast between first front edge 8 of chip 2 and the dark-shadowed depression 34. The height of depression 34 is preferably set above the bottom wall and below the top wall of chip terminal ends 10. It is preferred that the grayness of the shadow created in depression 34 differs by up to fifteen gray units, or by at least sixteen gray units, from the grayness of the front wall 5 of chip 2 on the Electronics Industry Association's standard gray scale. This gray scale is divided into 255 objectively different shades of gray ranging at one end of pure white to the other end of pure black and is recognized in the color industry. Depression 34 may be cut or drilled into chip-handling wheel 16 and its depth will depend on various factors such as the size and depth of cavity 13, and the size of chip 2. Depression 34 further may be circular (FIG. 7a), oval-shaped (FIG. 7b), or may be a horizontal slot (FIG. 7c) that extends away from cavity 13 in first wall 30. In yet another embodiment of this invention, FIG. 9 shows depression 34 extending along cavity side wall 24 and along cavity rear wall 26 to create a shadow therein that is eclipsed by second front edge 9 of chip 2. The shadow that is created forms an objectively measurable contrast in grayness between the shadow in rear wall 26 and chip 2.

Figure 10:
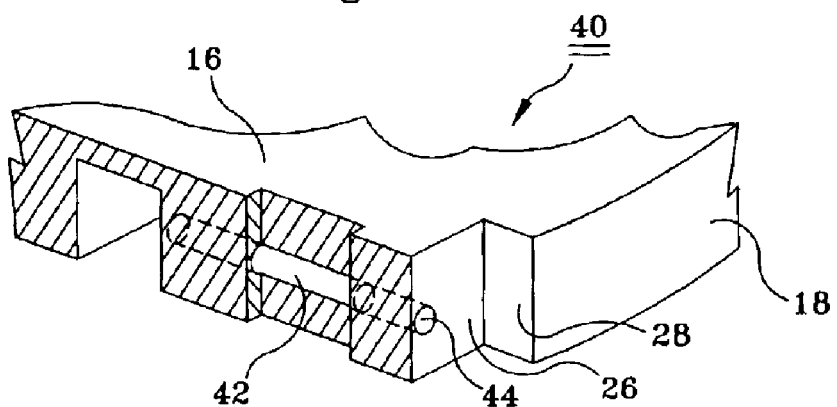
Figure 11:
FIG. 11 shows a 255-unit grayscale with exemplary 17 grayscale steps from black to white (0=black and 255=white) with an exemplary step value of 16.

As shown in FIG. 10, apparatus 12 may include a retaining means 40 for holding chip 2 momentarily in cavity 13 to allow inspection. Retaining means 40 includes a vacuum source (not shown) and vacuum transmission passage way 42 leading from the vacuum source to a vacuum slot 44 opening into within cavity 13. The vacuum assists holding chip 2 in cavity 13 during inspection.

A locating means (not shown) is provided for finding the chip seated within cavity 13. Locating means may include a charged-coupled device camera (not shown), for gathering and focusing the images of chip 2, and transmitting them to a nearby inspection device, such as a image processing unit (not shown), and a sufficient light source (not shown) for finding edge 8 of chip 2 where edge 8 eclipses darkshadowed depression 34. The line of contrast between depression 34 and chip 2 provides the point of reference for the inspection device to find chip 2 so that the inspection device can initiate the testing process.

While the invention has been described with reference to a particular embodiment thereof, those skilled in the art will be able to make various modifications to the described embodiment of the invention without departing from the true spirit and scope thereof. It is intended that all combinations of elements and steps which perform substantially the same function in substantially the same way to achieve substantially the same result are within the scope of this invention.

What is claimed is:

1. An apparatus for supporting a micro-electronic chip within a chip-holding cavity and establishing a location of the chip for optical inspection, the chip having at least a front wall and a pair of opposed, spaced-apart side walls, wherein the front wall meets with each of the side walls to form opposed, spaced-apart first and second front edges, comprising:

a microchip support structure having at least first and second chip holding cavities for holding respective first and second chips, wherein:

each of the first and second chip-holding cavities have a cavity side wall formed to juxtapositionally abut at least one of the side walls of the respective first and second chips;

the respective cavity side walls having intentionally formed therein a depression adapted for creating a shadow that has a measurable contrast in grayness with that of the first front edge of the respective first and second chips to form a detectable border between the shadow and the respective first and second chips; and, the depression in the cavity side wall of the first chipholding cavity is substantially identical to the depression in the cavity side wall of the second chip-holding cavity.

2. The apparatus of claim 1 wherein the first front edge of the chip forms a straight border with the shadow.

3. The apparatus of claim 1 wherein the first front edge of the chip forms a vertical border with the shadow.

4. The apparatus of claim 1 further including a vacuum retaining means for momentarily holding the chip within the cavity, said vacuum retaining means including a vacuum source and a vacuum transmission passage way leading from the vacuum source to the cavity for applying a vacuum against the chip to assist in holding the chip in the cavity.

5. The apparatus of claim 1 wherein the grayness of the shadow differs by from one up to fifteen gray units from the grayness of the front of the chip on an industrial, 255 unit, grayness scale.

6. The apparatus of claim 1 wherein the grayness of the shadow differs by at least sixteen gray units from the grayness of the front of the chip on an industrial, 255 unit, grayness scale.

7. The apparatus of claim 1 wherein the depression is circular.

8. The apparatus of claim 1 wherein the depression is oval-shaped.

9. The apparatus of claim 1 wherein the depression is a horizontal slot.

10. The apparatus of claim 1 wherein the cavity is bound by a cavity rear wall.

11. The apparatus of claim 10 wherein the depression extends along the cavity side wall and along the cavity rear wall to create a second shadow therein that is eclipsed by the second front edge of the chip, the second shadow created in the depression in the cavity rear wall forming a measurable contrast in grayness between the second shadow and the chip.

12. The apparatus of claim 1 in which surfaces surrounding the cavity comprise aluminum, stainless steel, titanium, or other metallic materials.

13. The apparatus of claim 1 in which the cavities are formed in a chip-handling wheel.

14. The apparatus of claim 13 in which the chip-handling wheel has a rim and the cavities are formed in the rim.

15. The apparatus of claim 1 in which the cavities are substantially larger than the chips.

16. The apparatus of claim 1 in which the apparatus is adapted for presenting one chip at-a-time for determination of its location within the cavity.

17. The apparatus of claim 1 in which the cavity side wall is partially formed into a first wall that extends away from the cavity and forms a recess located adjacent the side wall and the first front edge of the chip.

18. An apparatus for supporting a micro-electronic chip within a chip-holding cavity and establishing a location of the chip for optical inspection, the chip having at least a front wall and a pair of opposed, spaced-apart side walls, wherein the front wall meets with each of the side walls to form opposed, spaced-apart first and second front edges, comprising:

a chip-handling wheel having an outer rim;

a cavity side wall formed in the outer rim of the chiphandling wheel to juxtapositionally abut a portion of at least one of the side walls of the chip, the cavity side wall being partially formed into a first wall that extends away from the cavity and forms a recess located adjacent the side wall and the first front edge of the chip; and, the cavity side wall and the first wall having formed therein a depression for creating a shadow that has a measurable contrast in grayness with that of the first front edge of the chip to form a detectable border of between the shadow and the chip.

19. The apparatus of claim 18 wherein the first front edge of the chip forms a straight border with the shadow.

20. The apparatus of claim 18 wherein the first edge of the chip forms a vertical, straight border with the shadow.

21. The apparatus of claim 18 further including a vacuum retaining means for momentarily holding the chip within the cavity, wherein the retaining means includes a vacuum source and a vacuum transmission passage way leading from the vacuum source to the cavity for applying a vacuum against the chip to assist in holding the chip in the cavity.

22. The apparatus of claim 18 wherein the grayness of the shadow by from one up to fifteen gray units from the grayness of the front of the chip on the industrial, 255 unit, grayness scale.

23. The apparatus of claim 18 wherein the grayness of the shadow differs by at least sixteen units from the grayness of the front of the chip on the industrial, 255 unit, grayness scale.

24. The apparatus of claim 18 wherein the depression is circular.

25. The apparatus of claim 18 wherein the depression is oval-shaped.

26. The apparatus of claim 18 wherein the depression is a horizontal slot.

27. The apparatus of claim 18 wherein the cavity is bound by a cavity rear wall.

28. The apparatus of claim 18 wherein the depression extends along the cavity side wall and along the cavity rear wall to create a second shadow therein that is eclipsed by the second front edge of the chip, the second shadow created in the depression in the cavity rear wall forming a measurable contrast in grayness between the second shadow and the chip.

29. A method for determining a location of a micro-electronic chip for optical inspection in a cavity of a chip-handling apparatus, the chip-handling apparatus and the micro-electronic chip having high specularity values, the cavity having a cavity side wall and the micro-electronic chip having a chip front wall and an adjoining chip side wall that form a front edge, comprising:

receiving the chip in the cavity such that the chip side wall abuts the cavity side wall, the cavity side wall having a depression for creating a shadow that has a measurable contrast in grayness with that of chip front wall; and employing the grayness contrast between the shadow and the chip front wall to determine location of the front edge of the chip.

30. The method of claim 29 in which the front edge of the chip forms a straight border with the depression and provides a reference for optical inspection.

31. The method of claim 29 further comprising applying vacuum to retain the chip within the cavity.

32. The method of claim 29 in which the grayness contrast between the shadow and the chip front wall differ by at least sixteen gray units on an industrial 255 unit grayness scale.

33. The method of claim 29 in which the depression comprises a circular, oval, or slot-like shape.

34. The method of claim 29 in which the cavity includes a cavity rear wall that adjoins the cavity side wall and a cavity second side wall, and in which the cavity rear wall and/or cavity second side wall include another depression forming a second shadow having a grayness that is measurably different from grayness of a chip second side wall, a chip rear wall, or the chip front wall.

35. The method of claim 29 further comprising inspecting the chip for visible flaws while the chip is retained in the cavity.

36. The method of claim 29 in which the depression reduces specularity around an area of the chip that undergoes optical inspection.

37. The method of claim 35 in which the chip-handling apparatus comprises surfaces surrounding the cavity made from aluminum, stainless steel, titanium, or other metallic materials.

38. The method of claim 29 in which employing the grayness contrast between the shadow and the chip front wall to determine the location of the front edge of the chip further comprises:

providing sufficient light; and employing a camera.

39. The method of claim 29 in which the cavity is formed in a chip-handling wheel.

40. The method of claim 39 in which the chip-handling wheel has a rim and the cavity is formed in the rim.

41. The method of claim 29 in which the cavity is substantially larger than the chip.

42. The method of claim 29 in which one chip at-a-time is presented for determination of its location within the cavity.

43. The method of claim 29 in which the chip handling apparatus comprises:

a microchip support structure having at least first and second chip holding cavities for holding respective first and second chips, wherein:

each of the first and second chip-holding cavities have a cavity side wall formed to juxtapositionally abut at least one of the side walls of the respective first and second chips;

the respective cavity side walls having intentionally formed therein a depression adapted for creating a shadow that has a measurable contrast in grayness with that of the first front edge of the respective first and second chips to form a detectable border between the shadow and the respective first and second chips; and, the depression in the cavity side wall of the first chip-holding cavity is substantially identical to the depression in the cavity side wall of the second chip-holding cavity.

44. The method of claim 29 in which the cavity side wall is partially formed into a first wall that extends away from the cavity and forms a recess located adjacent the side wall and the first front edge of the chip.

* * * * *